(12) United States Patent
Hashino et al.

(10) Patent No.: US 9,375,359 B2
(45) Date of Patent: Jun. 28, 2016

(54) PANTS-TYPE ABSORBENT WEARING ARTICLE WITH BUTTOCKS COVERING PORTION

(75) Inventors: Yuki Hashino, Kagawa (JP); Shunsuke Masaki, Kagawa (JP)

(73) Assignee: Unicharm Corporation, Ehime (JP)

( * ) Notice: Subject to any disclaimer, the term of this patent is extended or adjusted under 35 U.S.C. 154(b) by 306 days.

(21) Appl. No.: 13/704,907

(22) PCT Filed: Jun. 27, 2011

(86) PCT No.: PCT/JP2011/064644
§ 371 (c)(1),
(2), (4) Date: Dec. 17, 2012

(87) PCT Pub. No.: WO2012/002308
PCT Pub. Date: Jan. 5, 2012

(65) Prior Publication Data
US 2013/0096528 A1 Apr. 18, 2013

(30) Foreign Application Priority Data
Jul. 1, 2010 (JP) ................................. 2010-151493

(51) Int. Cl.
*A61F 13/15* (2006.01)
*A61F 13/20* (2006.01)
(Continued)

(52) U.S. Cl.
CPC .............. *A61F 13/476* (2013.01); *A61F 13/496* (2013.01); *A61F 13/49011* (2013.01); *A61F 13/49466* (2013.01); *A61F 13/515* (2013.01)

(58) Field of Classification Search
CPC A61F 13/49011; A61F 13/496; A61F 13/539

USPC ................... 604/385.01, 385.28, 385.27, 398
See application file for complete search history.

(56) References Cited

U.S. PATENT DOCUMENTS 5,074,854 A * 12/1991 Davis ........................ 604/385.11
6,132,410 A * 10/2000 Van Gompel et al. ... 604/385.25
(Continued)

FOREIGN PATENT DOCUMENTS

EP     2 260 812 A1    12/2010
JP     2007-014538     1/2007
(Continued)

OTHER PUBLICATIONS

International Search Report based on PCT application No. PCT/JP2011/064644 dated Sep. 13, 2011 (4 pgs).
(Continued)

*Primary Examiner* — Michele M Kidwell
(74) *Attorney, Agent, or Firm* — Brinks Gilson & Lione

(57) ABSTRACT

A pants-type wearing article that provides effective buttocks covering having a front panel, a rear panel and a crotch panel connected to the front panel and the rear panel so as to cover a crotch region of the article wearer. The rear panel is formed with a rear waist covering portion having a dimension in the longitudinal direction substantially the same as a dimension of the front panel and a buttocks covering portion contiguously extending downward from the rear waist covering portion and adapted to cover at least partially the wearer's buttocks. The buttocks covering portion has buttock elastics extending in the transverse direction. The buttocks covering portion and the crotch panel are joined to each other in a zone defined between the gasket cuffs opposite to each other in the transverse direction and not joined to each other at portions in which the gasket cuffs are disposed.

10 Claims, 8 Drawing Sheets

(51) Int. Cl.
  *A61F 13/476*   (2006.01)
  *A61F 13/49*    (2006.01)
  *A61F 13/494*   (2006.01)
  *A61F 13/496*   (2006.01)
  *A61F 13/515*   (2006.01)

(56) References Cited

U.S. PATENT DOCUMENTS

| | | | | |
|---|---|---|---|---|
| 6,217,563 | B1 * | 4/2001 | Van Gompel et al. | 604/385.101 |
| 6,364,863 | B1 * | 4/2002 | Yamamoto | A61F 13/49009 604/385.27 |
| 7,150,729 | B2 * | 12/2006 | Shimada et al. | 604/385.01 |
| 8,905,990 | B2 * | 12/2014 | Malowaniec | 604/385.31 |
| 2002/0147439 | A1 * | 10/2002 | Tanaka | A61F 13/496 604/398 |

FOREIGN PATENT DOCUMENTS

| | | |
|---|---|---|
| JP | 2008-194161 | 8/2008 |
| JP | 2009-160128 | 7/2009 |
| JP | 2009-240640 | 10/2009 |
| JP | 2009-240695 | 10/2009 |
| JP | 4388136 B | 10/2009 |
| WO | WO 2007/144838 A1 | 12/2007 |
| WO | WO 2009/084643 A1 | 7/2009 |

OTHER PUBLICATIONS

European Supplemental Search Report from corresponding European application No. 11800772.3 dated Jan. 31, 2014 (7 pgs).

* cited by examiner

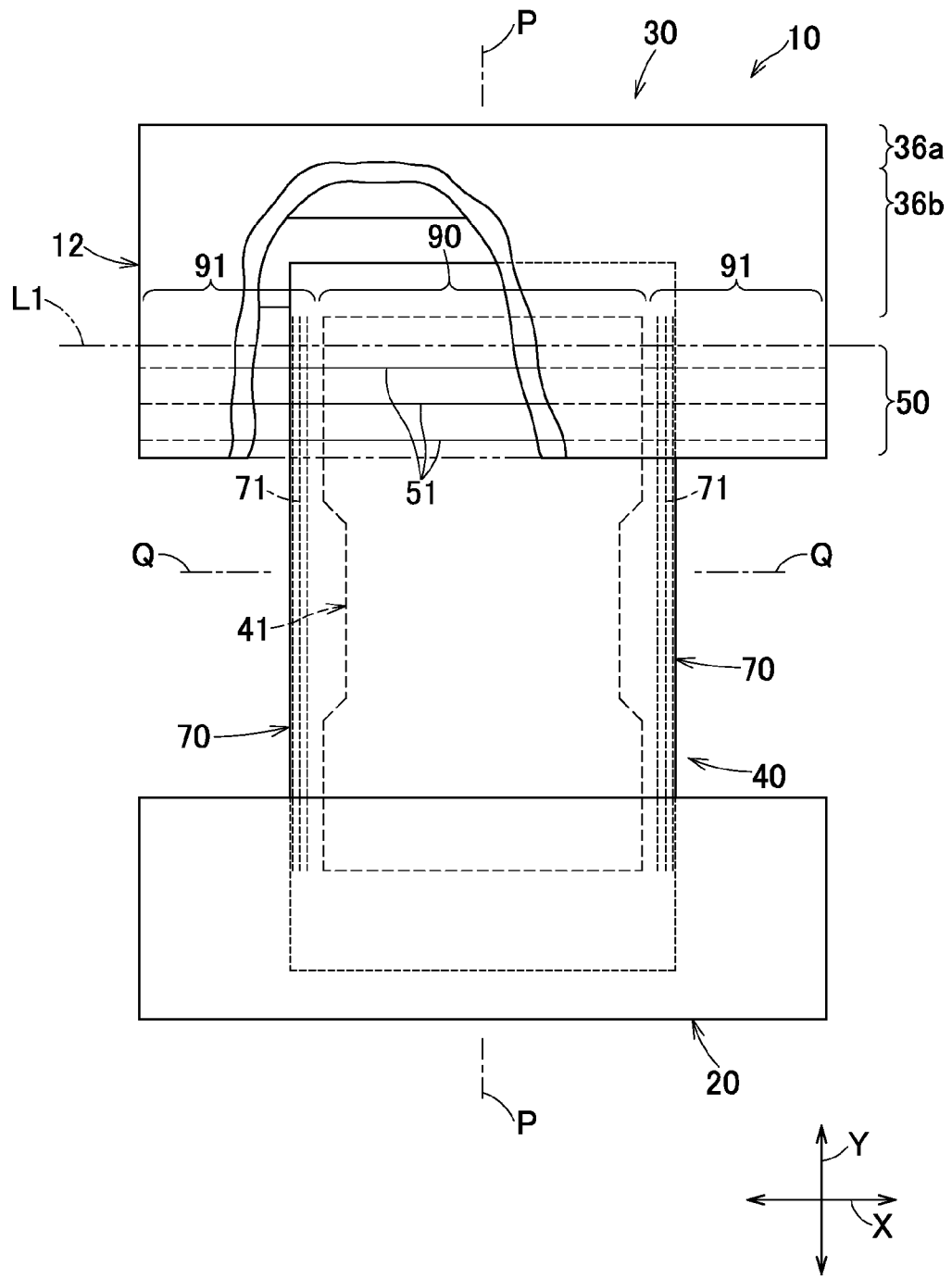

PANTS-TYPE ABSORBENT WEARING ARTICLE WITH BUTTOCKS COVERING PORTION

RELATED APPLICATION

This application is a 35 U.S.C. §371 national phase filing of International Patent Application No. PCT/JP2011/064644, filed Jun. 27, 2011, through which and to which priority is claimed under 35 U.S.C. §119 to Japanese Patent Application No. 2010-151493, filed Jul. 1, 2010.

TECHNICAL FIELD

The present invention relates to pants-type absorbent wearing articles and more specifically to pants-type absorbent wearing articles such as disposable diapers, toilet-training pants and incontinent briefs.

BACKGROUND

Conventionally, pants-type absorbent wearing articles composed of three members, i.e., a front waist member, a rear waist member and an absorbent member extending between the front and rear waist members are widely known.

For example, JP 2007-14538 A (PTL 1) discloses a technique relating to the pants-type diaper as follows:

(1) The front waist member is a front panel adapted to cover the wearer's front waist region. The rear waist member is a rear panel adapted to cover the wearer's rear waist region. The absorbent member is connected to the front panel and the rear panel to cover the wearer's crotch region.

(2) The rear panel is formed with a rear waist covering portion having a longitudinal dimension substantially the same as that of the front panel and a buttocks covering portion contiguously extending downward from the rear waist covering portion to cover at least partially the wearer's buttocks.

(3) The crotch panel is provided with an absorbent structure extending in a longitudinal direction to absorb body waste such as urine and gasket cuffs extending in the longitudinal direction and including gasket elastics which are elastically contractible in the longitudinal direction.

(4) The buttocks covering portion is provided with the buttock elastics extending along edges of the buttocks covering portion.

(5) The buttocks covering portion and the crotch panel are joined to each other at a zone in which the buttock elastics and the gasket elastics intersect with one another.

CITATION LIST

Patent Literature

{PTL 1}: JP 2007-14538 A

SUMMARY

Technical Problem

When the buttocks covering portion and the crotch panel are joined to each other in the intersecting zone of the buttock elastics and the gasket elastics, the contractile force of the gasket elastics acts on the buttocks covering portion. As a result, the buttocks covering portion is contracted in the longitudinal direction under the contractile force of the gasket elastics. Consequently, an effect area of the buttocks covering portion to cover the wearer's buttocks may be decreased.

An object of the present invention is to provide a pants-type wearing article adapted to inhibit a decrease in an effective area of a buttocks covering portion to cover the wearer's buttocks.

Solution to Problem

The present invention provides a pants-type absorbent wearing article having a longitudinal direction, a transverse direction and a front-back direction, and including a front panel adapted to cover a front waist region of the wearer, a rear panel adapted to cover a rear waist region of the wearer, and a crotch panel including an absorbent structure and being connected to the front panel and the rear panel to cover a crotch region of the wearer. The rear panel is formed with a rear waist covering portion having a dimension in the longitudinal direction substantially the same as that of the front panel and a buttocks covering portion contiguously extending downward from the rear waist covering portion and adapted to cover at least partially the wearer's buttocks. The absorbent structure includes an absorbent core extending in the longitudinal direction and gasket cuffs extending in the longitudinal direction along lateral portions of the absorbent structure and provided with gasket elastics adapted to be elastically contractible in the longitudinal direction. The buttocks covering portion is provided with buttock elastics extending in the transverse direction.

The buttocks covering portion and the crotch panel are joined to each other at a zone defined between the gasket cuffs extending along the lateral portions of the absorbent structure and not joined to each other in the respective gasket cuffs.

According to one embodiment of the present invention, the rear waist covering portion is provided with rear waist elastics adapted to be elastically contractible in the transverse direction; the crotch panel and the rear panel are joined to each other at a zone in which the gasket elastics and the rear waist elastics intersect with each other; the front panel is provided with front waist elastics adapted to be elastically contractible in the transverse direction; and the crotch panel and the front panel are joined to each other at a zone in which the gasket elastics and the front waist elastics intersect with one another.

According to another embodiment of the present invention, the buttock elastics are secured under no tension to the rear panel.

According to even another embodiment of the present invention, the buttock elastics are secured under no tension to the rear panel at least at a portion in which the buttocks covering portion and the absorbent structure overlap with each other.

According to still another embodiment of the present invention, when a piece including a single buttock elastic and a piece including a single rear waist elastic both having a same dimension in the transverse direction are cut out from the buttocks covering portion and the rear waist covering portion, a dimension in the transverse direction of the buttocks covering portion in its contracted state is larger than a dimension in the transverse direction of the rear waist covering portion in its contracted state.

According to yet another embodiment of the present invention, when a piece including a single buttock elastic and a piece including a single rear waist elastic both having a same dimension in the transverse direction are cut out from the buttocks covering portion and the rear waist covering portion, a dimension in the transverse direction of the buttocks covering portion in its contracted state is substantially the same as a dimension in the transverse direction of the rear waist covering portion in its contracted state and intervals in the longitudinal direction of the buttock elastics are larger than intervals in the longitudinal direction of the rear waist elastics.

According to further another embodiment of the present invention, the rear waist elastics are contractible in the transverse direction in the lateral edges of the absorbent structure.

According to an additional embodiment of the present invention, a range in which the rear waist elastics are contractible in the lateral edges of the absorbent structure is 5 to 20% of the dimension in the transverse direction of the absorbent structure.

Advantageous Effects of Invention

In the pants-type absorbent wearing article according to the present invention, the buttocks covering portion and the crotch panel are not joined to each other in the respective gasket cuffs in the transverse direction and therefore it is possible to inhibit the contractile force of the gasket elastics acting on the buttocks covering portion. In consequence, the contraction of the buttocks covering portion in the longitudinal direction under the contractile force of the gasket elastics can be inhibited and thereby a decrease of the effective area of the buttocks covering portion to cover the wearer's buttocks can be inhibited.

Further, the buttocks covering portion and the crotch panel are joined to each other at the zone defined between the gasket cuffs opposite to each other in the transverse direction, whereby the absorbent structure is unlikely to move relative to the buttocks covering portion.

BRIEF DESCRIPTION OF DRAWINGS

FIG. 9 is a developed plan view illustrating a variant of the diaper.

DESCRIPTION OF EMBODIMENTS

FIGS. 1 through 8 illustrate a disposable diaper (referred to hereunder simply as "diaper") as an example of a pants-type absorbent wearing article according to the present invention. In these accompanying drawings, X indicates a transverse direction, Y indicates a longitudinal direction being orthogonal to the transverse direction X and Z indicates a front-back direction being orthogonal to the transverse direction X and the longitudinal direction Y, respectively. Line P-P indicates a longitudinal imaginary center line, line Q-Q indicates a transverse imaginary center line and line L1 indicates a transverse imaginary boundary line. This diaper 10 is formed symmetrically about the longitudinal imaginary center line P-P bisecting a dimension of the diaper 10 in the transverse direction X.

Figure 1:
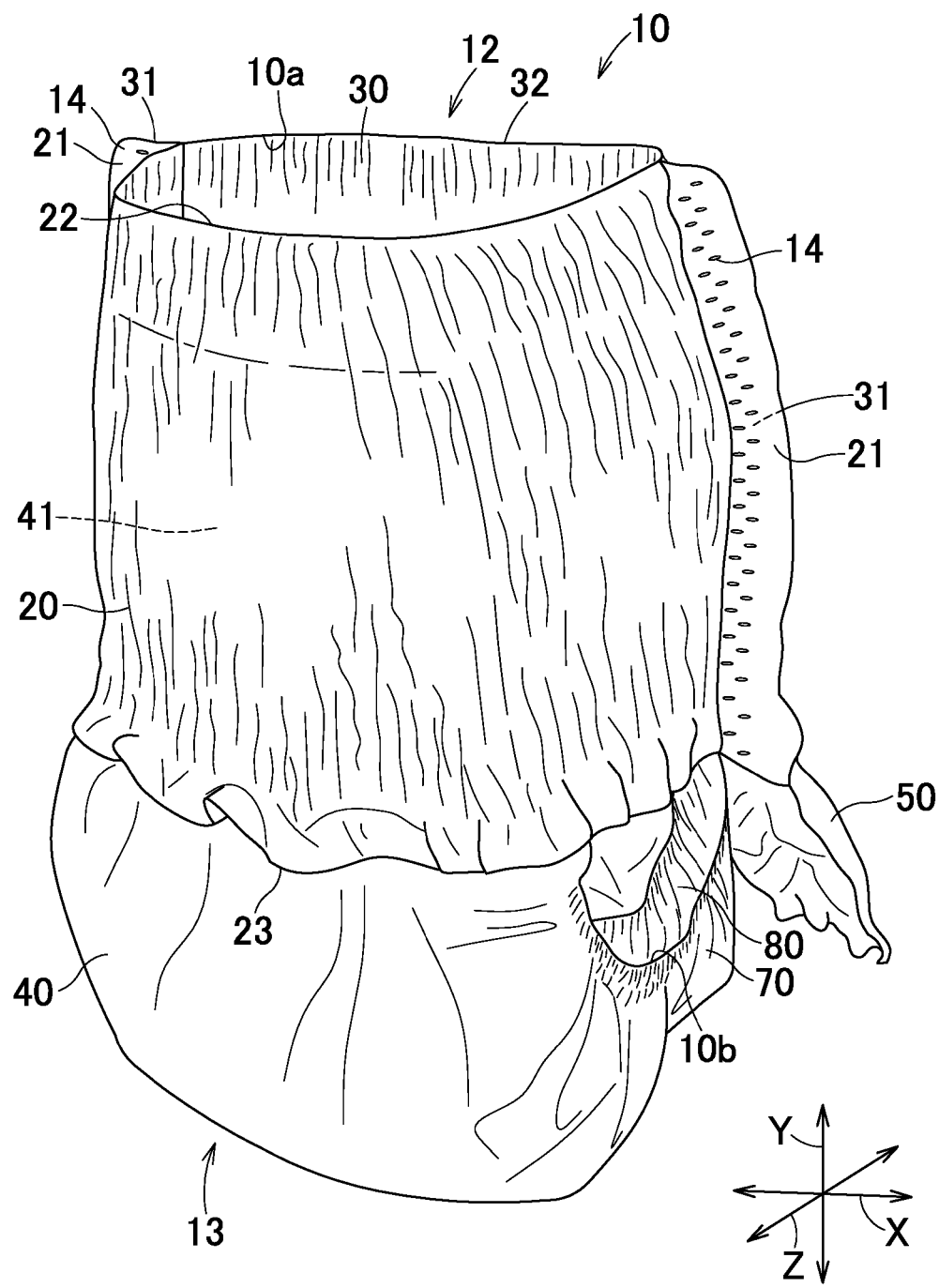
FIG. 1 is a perspective view of a disposable diaper as an example of a pants-type absorbent wearing article.

FIG. 1 is a elevational perspective view illustrating the diaper 10 with a waist-opening 10a and a leg-openings 10b being in an opened state as viewed from the front side thereof.

This diaper 10 is formed of three panels 20, 30, 40, i.e., a front panel 20, a rear panel 30 and a crotch panel 40.

Figure 2:
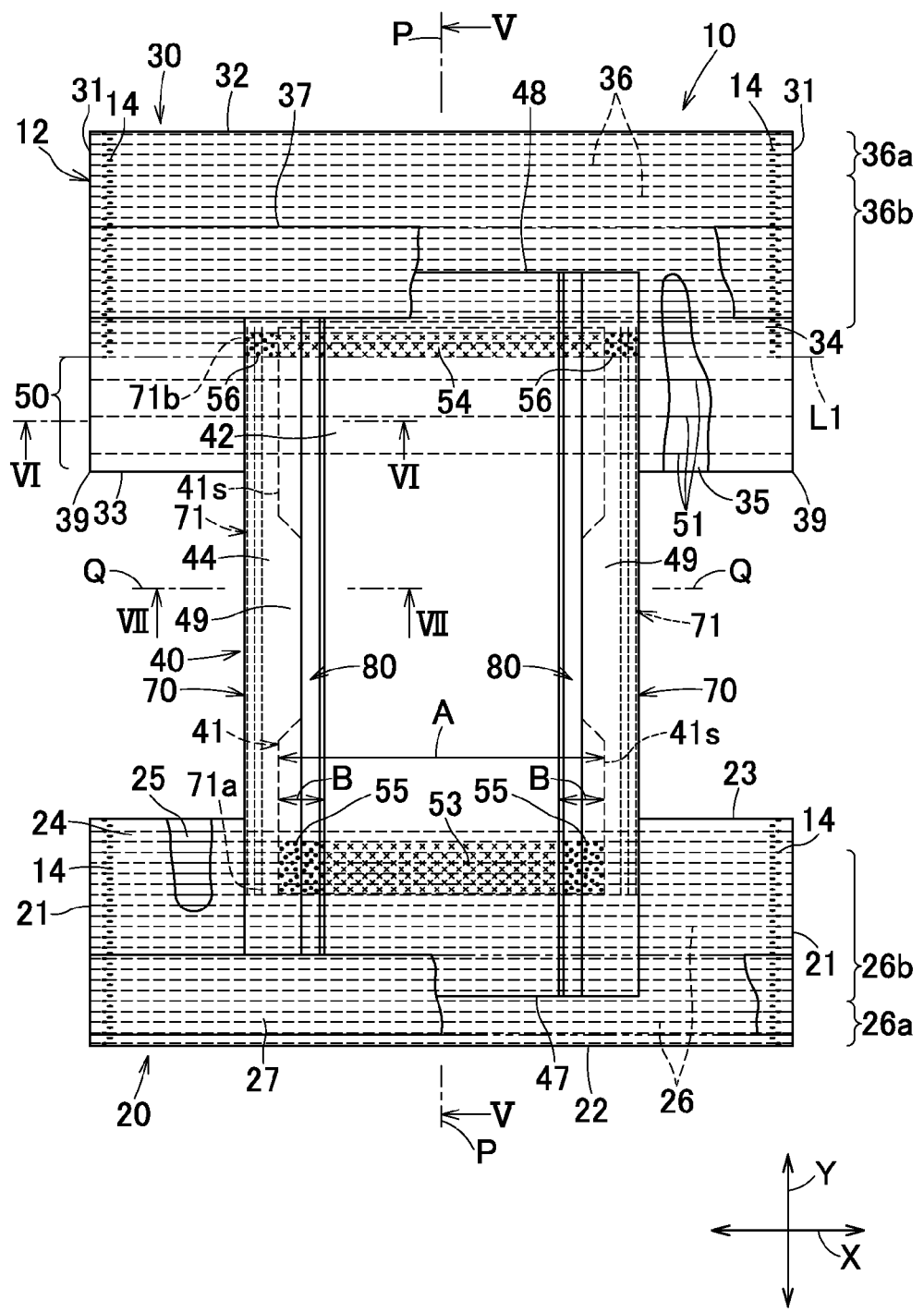
FIG. 2 is a developed plan view of the diaper as viewed from the side of a skin-facing surface thereof.
Figure 3:
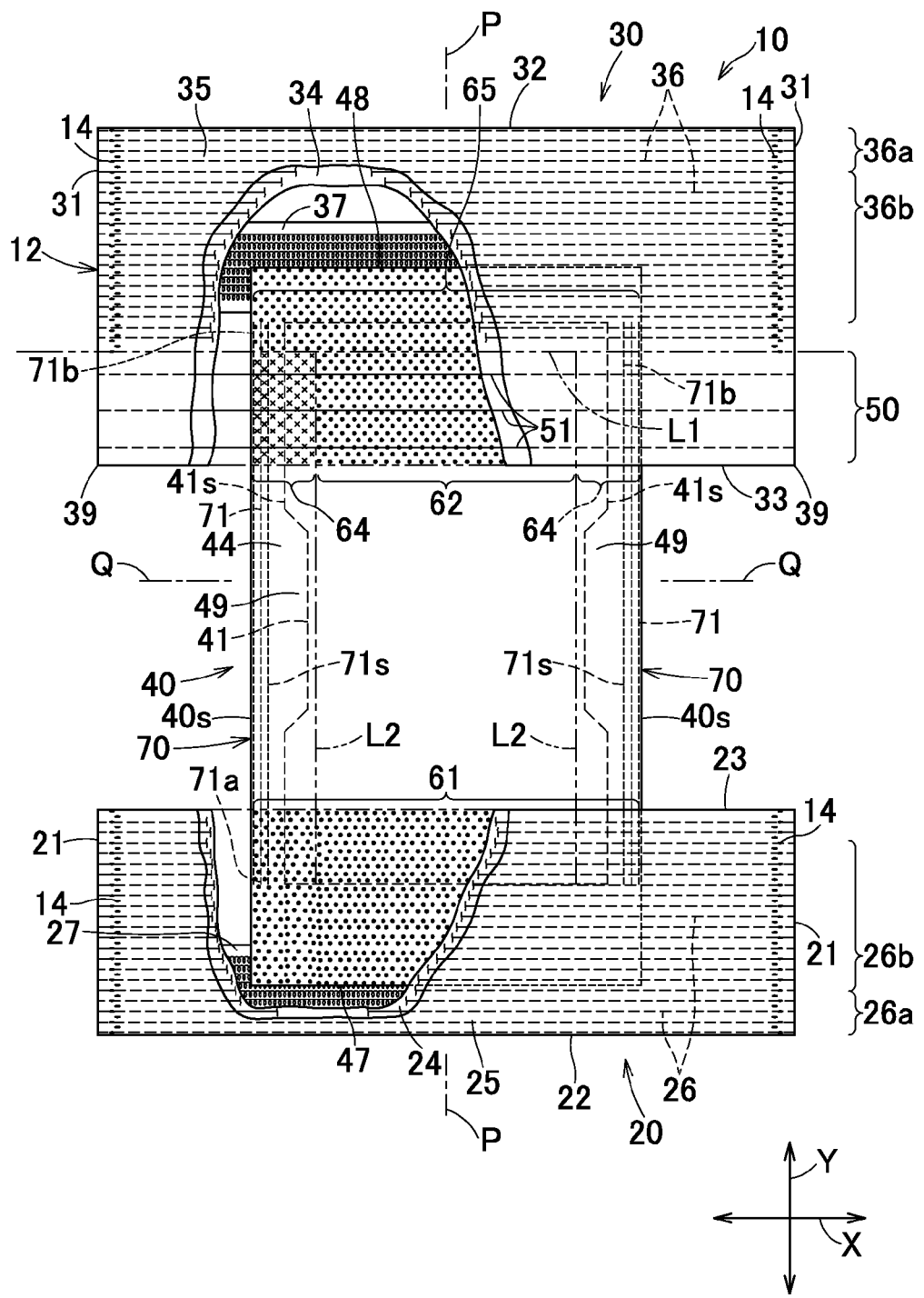
FIG. 3 is a developed plan view of the diaper as viewed from the side of a non-skin-facing surface thereof.

FIG. 2 illustrates the diaper 10 developed, after the front and rear panels 20, 30 have been separated off from each other, by stretching respective elastics of the diaper 10 described below against contractile force thereof as viewed from the side of the skin-facing surface and FIG. 3 illustrate the diaper 10 in this state as viewed from the non-skin-facing surface.

The front and rear panels 20, 30 are separated from each other in the longitudinal direction Y and extend in the transverse direction X as well as in the longitudinal direction Y, respectively. These front and rear panels 20, 30 may be joined to each other along front panel lateral edges 21 and the rear panel lateral edges 31 to form a series of seams 14 as seen in FIG. 1 and to form the waist-opening 10a and a pair of the leg-openings 10b.

As illustrated in FIGS. 2 and 3, the front panel 20 includes a front inner sheet 24 and a front outer sheet 25 each having a rectangular shape, front waist elastics 26 and a front cover sheet 27 wherein the front waist elastics 26 are secured between the front inner sheet 24 and the front outer sheet 25. The front inner sheet 24 and the front outer sheet 25 have substantially the same dimensions in the longitudinal direction Y and in the transverse direction X, respectively.

An arrangement of the front waist elastics 26 is the same as an arrangement of rear waist elastics 36 to be described hereinafter and therefore the arrangement of the front waist elastics 26 will be described later together with a description of the rear waist elastics 36.

This front panel 20 is adapted to cover the front waist region of the wearer.

The rear panel 30 includes a rear inner sheet 34 and a rear outer sheet 35 each having a rectangular shape, rear waist elastics 36, buttock elastics 51 and a rear cover sheet 37 wherein the rear waist elastics 36 and the buttock elastics 51 are secured between the rear inner sheet 34 and the rear outer sheet 35.

A dimension in the transverse direction X of the rear panel 30 is substantially the same as that of the front panel 20. Meanwhile, a dimension in the longitudinal direction Y of the rear panel 30 is larger than a dimension in the longitudinal direction Y of the front panel 20. Specifically, the rear panel 30 is formed with a rear waist covering portion 12 defined in the longitudinal direction Y by the transverse imaginary boundary line L1 and having a dimension in the longitudinal direction Y substantially the same as that of the front panel 20, and the buttocks covering portion 50 extending downward from the rear waist covering portion 12.

The rear waist covering portion 12 is adapted to cover the rear waist region of the wearer and the buttocks covering portion 50 is adapted to cover the buttocks of the wearer at least partially.

As materials of the sheets 24, 25, 34, 35, breathable and liquid-impermeable fibrous nonwoven fabrics, for example, an SMS nonwoven fabric, a spunbonded nonwoven fabric, a point-bonded nonwoven fabric and an air-through nonwoven fabric each having a mass per unit area in a range of about 10 to about 25 g/m$^2$ may be used. The inner sheets 24, 34 and the outer sheets 25, 35 may be formed of the same material or may be formed of different materials.

Respective dimensions in the longitudinal direction Y of the front panel 20 and the rear waist covering portion 12 are preferably in a range of about 70 to about 150 mm and more preferably of about 105 mm. A dimension in the longitudinal direction Y of the buttocks covering portion 50 is preferably in a range of about 30 to about 90 mm and more preferably of about 60 mm. With the dimensional relationship as has described above, during use of the diaper 10, the buttocks covering portion 50 extends downward from the lower end of the rear waist covering portion 12 to the lower ends defining parts of the respective leg-openings 10b to surround the respective leg-openings 10b partially and the lower end of the buttocks covering portion 50 is located at the level in the longitudinal direction Y lower than rear ends of gasket cuffs 70 and containment cuffs 80 both described later as shown in FIG. 2.

As materials of the front waist elastics 26 and the rear waist elastics 36, thread, string or strand elastics may be used, and these are contractibly secured under tension in the transverse direction X between the front inner and outer sheets 24, 25 and between the rear waist inner and outer sheets 34, 35, respectively. These front and rear waist elastics 26, 36 respectively extend in the transverse direction X and arranged at predetermined intervals in the longitudinal direction Y between the front inner and outer sheets 24, 25 and between the rear waist inner and outer sheets 34, 35, respectively. The interval in the longitudinal direction Y between each pair of adjacent elastics in the front and rear waist elastics 26, 36 is preferably in a range of about 4 to about 10 mm.

The front waist elastics 26 are divided into a group lying on the side of the waist-opening 10a to define a front first elastic zone 26a and a group lying on the side of the leg-openings 10b to define a front second elastic zone 26b. In a similar fashion, the rear waist elastics 36 are divided into a group lying on the side of the waist-opening 10a to define a rear first elastic zone 36a and a group lying on the side of the leg-openings 10b to define a rear second elastic zone 36b.

During use of the diaper 10, the front first elastic zone 26a is located in vicinities of the upper portion of the diaper in the longitudinal direction Y, i.e., in vicinities of the waist-opening 10a and, in a flatly developed state of the diaper 10, the front first elastic zone 26a is located in vicinities of a front outer end 22 of the front panel 20. In this embodiment, referring to FIGS. 2 and 3, for example, four of the front waist elastics 26 arranged at the predetermined intervals from the front outer end 22 of the front panel 20 upwardly in the longitudinal direction Y may define the front first elastic zone 26a and the remaining front waist elastics 26 may define the front second elastic zone 26b.

During use of the diaper 10, the rear first elastic zone 36a is located in vicinities of the upper portion of the diaper in the longitudinal direction Y, i.e., in vicinities of the waist-opening 10a and, in the flatly developed state of the diaper 10, the rear first elastic zone 36a is located in vicinities of a rear outer end 32 of the rear waist covering portion 12. In this embodiment, referring to FIGS. 2 and 3, for example, four of the rear waist elastics 36 arranged at the predetermined intervals from the rear outer end 32 of the rear waist covering portion 12 downwardly in the longitudinal direction Y may define the rear first elastic zone 36a and the remaining rear waist elastics 36 may define the rear second elastic zone 36b.

During use of the diaper 10, these front and rear first elastic zones 26a, 36a primarily function to prevent the diaper 10 from slipping down along the wearer's body. The front and rear second elastic zones 26b, 36b primarily function to prevent the diaper 10 from being spaced apart from the wearer's body. The function of the front and rear first elastic zones 26a, 36a and the function of the front and rear second elastic zones 36a, 36b reinforce each other.

The front and rear first elastic zones 26a, 36a may have substantially the same contractile force or one of the front and rear first elastic zones 26a, 36a may have a contractile force higher than that of the other. This is true for the front and rear second elastic zones 26b, 36b. With respect to the contractile force, a specific aspect thereof will be described later in more detail.

As materials of the front and rear waist elastics 26, 36, it may be preferable to use seven to thirty-seven thread, string or strand elastics having a fineness in a range of about 310 to about 1240 dtex. According to the illustrated embodiment, twenty thread, string or strand elastics each having a fineness of about 470 dtex are used as the front and rear waist elastics 26, 36, respectively. These front and rear waist elastics 26, 36 may be contractibly secured under tension at an elongation ratio in a range of about 2.0 to about 3.4 between the front inner and outer sheets 24, 25 and between the rear waist inner and outer sheets 34, 35, respectively. According to the illustrated embodiment, the front and rear waist elastics 26, 36 defining the front and rear first elastic zones 26a, 36a are contractibly secured under tension, for example, at an elongation ratio of 2.3 between the front inner and outer sheets 24, 25 and between the rear waist inner and outer sheets 34, 35. The front waist elastics 26 defining the front second elastic zone 26b are secured under tension, for example, at an elongation ratio of 2.8 between the front inner and outer sheets 24, 25 and the rear waist elastics 36 defining the rear second elastic zone 36b are contractibly secured under tension, for example, an elongation ratio of 3.2 between the rear waist inner and outer sheets 34, 35.

With respect to the elongation ratio of the elastics, assuming that an elastic of 100 mm in a non-stretched state is stretched to a length of 200 mm and secured to a sheet, it will be described that the elastic is secured under tension at an elongation ratio of "2.0" to the sheet.

Portions of the front and rear waist elastics 26, 36 overlapping the crotch panel 40 are contractible in the transverse direction X only in lateral edges 41s of an after-mentioned absorbent core 41. More specifically, referring to FIG. 2, the portions of the front and rear waist elastics 26, 36 are provided in respective midsections in the transverse direction X of these portions with front and rear non-contractible zones 53, 54 adapted to be not subjected to the contractile force of the front and rear waist elastics 26, 36, respectively, and provided in the lateral portions in the transverse direction X of these front and rear non-contractile zones 53, 54 substantially overlapping after-mentioned containment cuffs 80 with front and rear contractile zones 55, 56 adapted to be subjected to the contractile force of the front and rear waist elastics 26, 36, respectively. In FIG. 2, the front and rear contractile zones 55, 56 are indicated by dots and the front and rear non-contractile zones 53, 54 are indicated by crosses.

The front and rear non-contractile zones 53, 54 are free from the contractile force of the front and rear waist elastics 26, 36 and, as a result, the contraction of the absorbent core 41 in the transverse direction X is inhibited. In this way, it is possible to prevent the area of the absorbent core 41 to absorb body waste such as urine, to prevent creating an uncomfortable feeling against the wearer and, in addition, to prevent body waste from leaking out the diaper 10.

In contrast, the front and rear contractile zones 55, 56 are subjected to the contractile force of the front and rear waist elastics 26, 36 to put the containment cuffs 80 in close contact with the wearer's body.

According to the illustrated embodiment, two of the rear waist elastics 36 arranged above the transverse imaginary boundary line L1 as viewed in the longitudinal direction Y in FIG. 2 overlap with the absorbent core 41 and six of the front waist elastics 26 arranged below the transverse imaginary center line Q as viewed in the longitudinal direction Y in FIG. 2 overlap with the absorbent core 41. These front and rear waist elastics 26, 36 are appropriately treated so that the contractile force thereof may not act on the lateral edges 41s of the absorbent core 41 and thereby the front and rear non-contractile zones 53, 54 are formed. To define the front and rear non-contractile zones 53, 54 free from the contractile force of the front and rear waist elastics 26, 36, for example, the front and rear waist elastics 26, 36 may be secured to the front and rear panels 20, 30 to extend fully from respective one of the front and rear lateral edges 21, 31 in the transverse direction X thereof to respective other and thereafter the front and rear waist elastics 26, 36 of the front and rear non-contractile zones 53, 54 may be cut back or cut out or subjected to a deteriorating treatment or none of the front and rear waist elastics may be provided in the front and rear non-contractile zones 53, 54.

A dimension B in the transverse direction X of the front and rear contractile zones 55, 56 is preferably in a range of about 5 to about 20% of a dimension A in the transverse direction X of the absorbent core 41.

If the dimension of the front and rear contractile zones 55, 56 is smaller than the range as described above, it will be difficult to keep the containment cuffs 80 in close contact with the wearer's body and if this dimension is larger than the above-mentioned range, it is apprehended that the dimension A in the transverse direction X of the absorbent core 41 might be unacceptably reduced.

An example of relationship between the dimension A in the transverse direction X of the absorbent core 41 and the dimension B in the transverse direction X of the front and rear contractile zones 55, 56 is indicated in TABLE 1.

TABLE 1

| | Dimension A in transverse direction X of absorbent core 41 | Contractible dimension B in transverse direction X of one of lateral edges 40s of absorbent core 41 | Percentage of dimension A to dimension B (%) |
|---|---|---|---|
| Diaper S | 120 mm | 20 mm | 16.7% |
| Diaper M | 120 mm | 10 mm | 8.3% |
| Diaper L | 120 mm | 15 mm | 12.5% |

According to the illustrated embodiment, the dimension in the transverse direction X of the respective front and rear contractile zones 55, 56 is substantially the same in respective lateral portions.

As a material of the buttock elastics 51, thread, string or strand elastics may be used and secured under tension so that the contractile force thereof may be utilized. The buttock elastics 51 may respectively extend in the transverse direction X and may be secured between the rear inner and outer sheets 34, 35 to be arranged at predetermined intervals in the longitudinal direction Y. According to the illustrated embodiment, the buttocks covering portion 50 is provided with three buttock elastics 51. The contractile force of buttock elastics 51 functions to put the buttocks covering portion 50 back to its initial state even if the buttocks covering portion 50 rides up due to movements of the wearer. An interval between each pair of the adjacent buttock elastics 51 in the longitudinal direction Y is preferably in a range of about 15 to about 30 mm.

As a material of the buttock elastics 51, one to four thread, string or strand elastics each having a fineness in a range of about 310 to about 1240 dtex may be preferably used. According to the illustrated embodiment, three buttock elastics 51 each having a fineness of about 470 dtex are used. The buttock elastics 51 are contractibly secured under tension at an elongation ratio in a range of about 1.5 to about 3.0 between the rear waist inner and outer sheets 34, 35 so that the contractile force of these elastics may act upon the buttocks covering portion. According to the illustrated embodiment, the one of the buttock elastics 51 lying closest to the transverse imaginary boundary line L1 is secured under tension at the elongation ratio of about 2.1, the remaining two of the buttock elastics 51 are contractibly secured under tension at the elongation ratio of about 1.9, respectively, between the rear waist inner and outer sheets 34, 35.

The contractile force of the buttocks covering portion 50 in the transverse direction X is set to be lower than that of the rear waist covering portion 12.

Now it is assumed that an elastic member under tension is secured to a sheet having a length dimension of 200 mm and the part of the sheet including a full length of this elastic under tension is cut out from the sheet. If a length dimension of the sheet in a state of contraction is 100 mm, it is assumed here that the contractile force of the elastic is "2.0" and if a length dimension of the sheet in a state of contraction is 50 mm, it is assumed that the contractile force of the elastic is "4.0". In other words, if a certain one of the same length dimensioned pieces cut off from the diaper 10 has a relatively low contractile force means that a length dimension of this piece in the state of contraction is relatively large.

According to the illustrated embodiment, when pieces having the same dimension in the transverse direction X are cut off from the buttocks covering portion 50 inclusive of one buttocks elastic 51 and the rear waist covering portion 12 inclusive of one rear waist elastics 36, the dimension in the transverse direction X of the buttocks covering portion 50 in the state of contraction is larger than the dimension in the transverse direction X of the rear waist covering portion 12 in the state of contraction.

The contractile force of the buttocks covering portion 50 in the transverse direction X is set to be weaker than the contractile force of the rear waist covering portion 12 in this manner for the reason that it is not necessary for the buttocks covering portion 50 to put in close contact with the wearer's body under a strong contractile force. If the contractile force of the buttocks covering portion 50 is set to be strong, the buttocks covering portion 50 will be curled up and an area over which the buttocks covering portion 50 could cover will be reduced. According to the illustrated embodiment, the intervals of the buttock elastics 51 in the longitudinal direction Y are set to be larger than the intervals in the longitudinal direction Y of the rear waist elastics 36 and thereby the above-mentioned problem can be further reliably overcome.

The buttock elastics 51 are secured between the rear waist inner and outer sheets 34, 35 with an adhesive directly applied to circumferential surfaces of the respective elastics 51. The rear waist inner and outer sheets 34, 35 also are joined to each other with an adhesive applied to the buttock elastics 51. Similarly to the buttock elastics 51, the front and rear waist elastics 26, 36 also are secured between the front inner and outer sheets 24, 25 and between the rear waist inner and outer sheets 34, 35. In this regard, it is also possible to secure these elastics 51, 26, 36 between the associated pairs of sheets with an adhesive applied to the respective sheets 24, 25, 34, 35.

Figure 4:
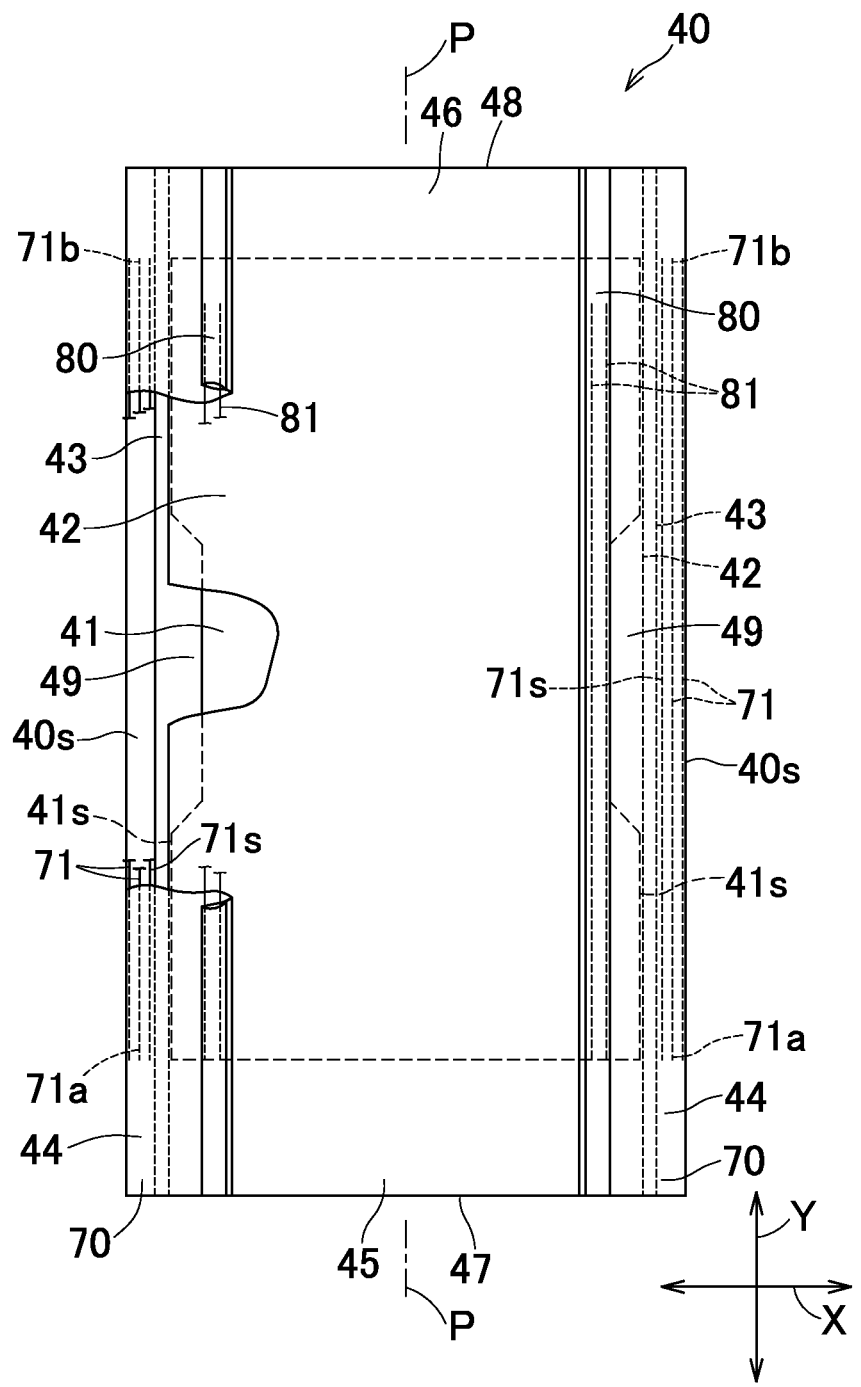
FIG. 4 is a detailed diagram illustrating a crotch panel.
Figure 5:
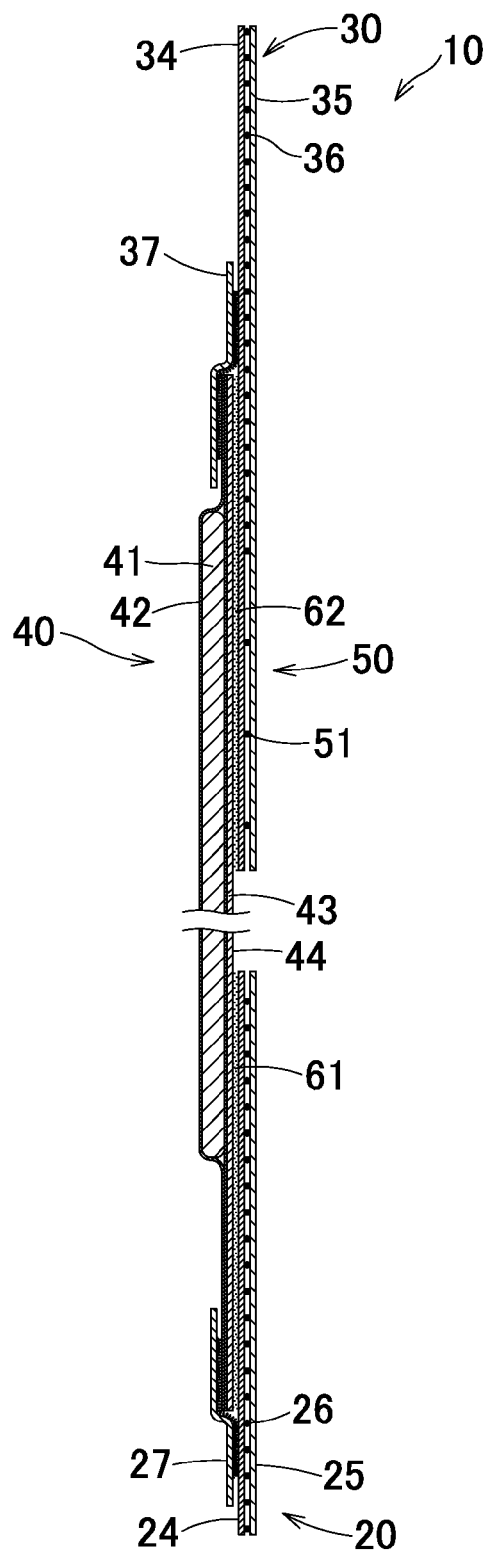
FIG. 5 is a sectional view taken along line V-V in FIG. 2.
Figure 6:
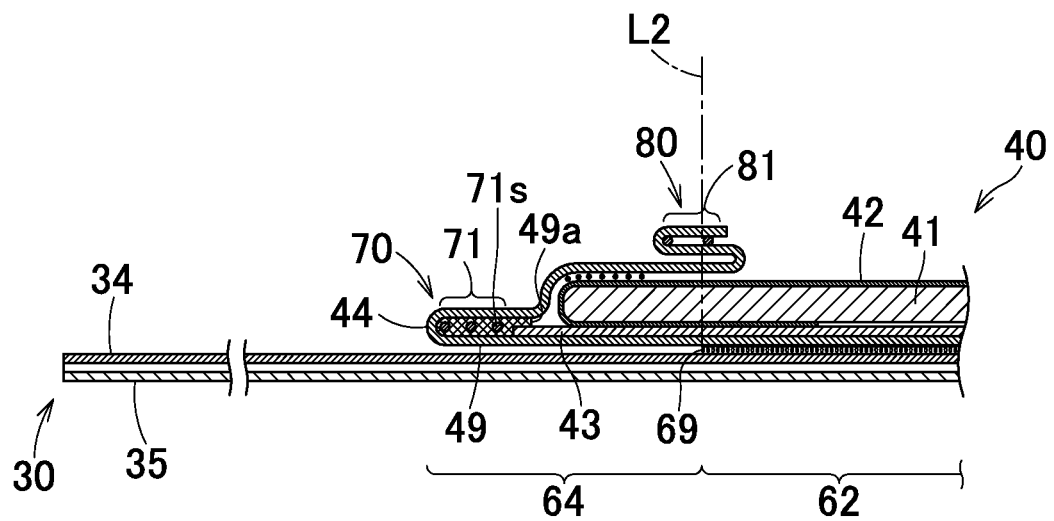
FIG. 6 is a sectional view taken along line VI-VI in FIG. 2.
Figure 7:
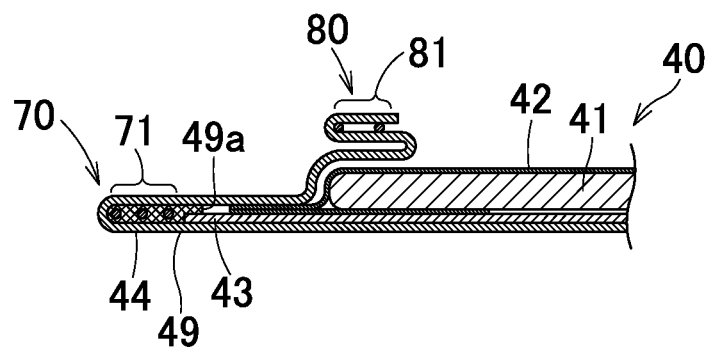
FIG. 7 is a sectional view taken along line VII-VII in FIG. 2.
Figure 8:
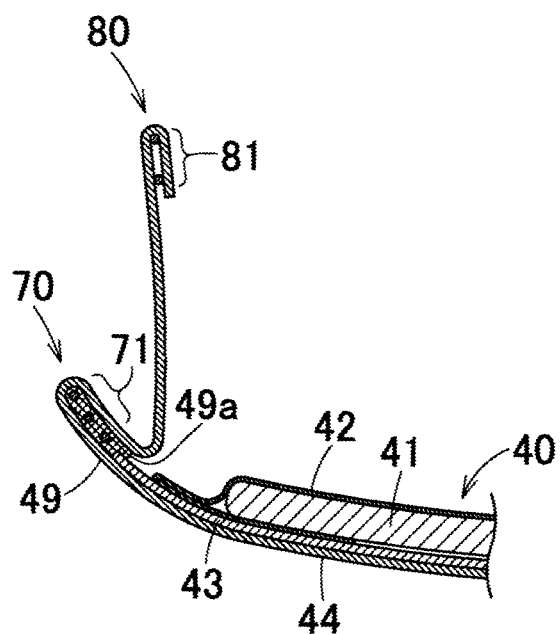
FIG. 8 is a diagram illustrating a change in the state of FIG. 7 under contraction of elastics.

FIG. 4 is a diagram illustrating the crotch panel 40 in detail, FIG. 5 is a sectional view taken along line V-V in FIG. 2, FIG. 6 is a sectional view taken along line VI-VI in FIG. 2 and FIG. 7 is a sectional view taken along line VII-VII in FIG. 2.

As illustrated in FIG. 4 through FIG. 7, the crotch panel 40 constituting an absorbent structure includes the absorbent core 41 adapted to absorb the wearer's bodily fluids such as urine, an inner sheet 42 adapted to cover the skin-facing surface of the absorbent core 41, a leakage-barrier sheet 43 adapted to cover the non-skin-facing surface of the absorbent core 41 and a bottom sheet 44 adapted to cover the non-skin-facing surface of the leakage-barrier sheet 43. In the form of such assembly of the respective constituents, the crotch panel 40 covers the wearer's crotch region.

The absorbent core 41 includes a mixture of fluff pulp fibers and superabsorbent polymer particles. The absorbent core 41 is concaved at lateral edges thereof in the vicinity of the transverse imaginary center line Q as illustrated in FIGS. 2 and 3.

As a material of the inner sheet 42, for example, a liquid-permeable fibrous nonwoven fabric may be used. As this inner sheet 42, for example, an air-through fibrous nonwoven fabric, a point-bonded fibrous nonwoven fabric or a spun-bonded fibrous nonwoven fabric having a mass per unit area in a range of about 10 to about 30 g/m$^2$ may be used. The leakage-barrier sheet 43 may be formed of liquid-impermeable plastic film so as to cover at least the entire non-skin-facing surface of the absorbent core 41 and thereby to prevent body waste, for example, urine from leaking toward the side of the non-skin-facing surface of the diaper 10.

A dimension in the longitudinal direction Y of the inner sheet 42 and the leakage-barrier sheet 43 is larger than a dimension in the longitudinal direction Y of the absorbent core 41, referring to FIG. 4, and therefore the absorbent core 41 is not present in front and rear ends 47, 48 of the crotch panel 40 as viewed in the longitudinal direction Y. Specifically, these front and rear ends 47, 48 are defined exclusively by the inner sheet 42 and the leakage-barrier sheet 43. In these front and rear ends 47, 48, the inner sheet 42 and the leakage-barrier sheet 43 are directly joined to each other by bonding means such as a hot melt adhesive.

A dimension in the transverse direction X of the inner sheet 42 and the leakage-barrier sheet 43 is also larger than a dimension in the transverse direction X of the absorbent core 41, referring to FIGS. 4, 6, 7 and 8, and these sheets 42, 43 extend outward beyond the lateral edges of the absorbent core 41 so as to define a pair of side flaps 49. These side flaps 49 extend in the longitudinal direction Y along lateral portions of the crotch panel 40.

The crotch panel 40 has the front and rear cover sheets 27, 37 which are relatively long in the transverse direction and attached thereto so as to cover the front and rear ends 47, 48 of the crotch panel 40 from the side of the skin-facing surface thereof, as illustrated in FIGS. 2 and 3. The front and rear cover sheets 27, 37 extend in the transverse direction X between the respective lateral edges 21, 31 of the front and rear panels 20, 30, respectively so as to cover the respective entire areas of the front and rear ends 47, 48 of the crotch panel 40. By covering the front and rear ends with the front and rear cover sheets 27, 37, respectively, in this manner, it is possible to prevent the constituent materials of the absorbent core 41 from falling off and, to prevent skin trouble due to contact of the front and rear ends 47, 48 with the wearer's skin.

As a material of the bottom sheet 44, for example, a breathable but liquid-impermeable fibrous nonwoven fabric may be used. Specifically, the bottom sheet 44 may be formed with use of, for example, a spunbonded/meltblown/spunbonded (SMS) fibrous nonwoven fabric, a point-bonded fibrous nonwoven fabric or a spunbonded fibrous nonwoven fabric each having a mass per unit area in a range of about 10 to about 25 g/m$^2$.

A dimension in the longitudinal direction Y of the bottom sheet 44 is, referring to FIG. 4, substantially the same as a dimension in the longitudinal direction Y of the inner sheet 42 and the leakage-barrier sheet 43. A dimension in the transverse direction X of the bottom sheet 44 is, referring to FIGS. 4, 6, 7 and 8, larger than a dimension in the transverse direction X of the absorbent core 41 and also than a dimension in the transverse direction X of the inner sheet 42 and the leakage-barrier sheet 43 so that respective segments of the bottom sheet 44 extending outward in the transverse direction X beyond the respective lateral edges of the inner sheet 42 and the leakage-barrier sheet 43 define the gasket cuffs 70 and the containment cuffs 80.

The gasket cuffs 70 are provided along the lateral edges in the transverse direction X of the absorbent core 41, respectively. More specifically, on the outer side in the transverse direction X of the absorbent core 41, the lateral portions of the bottom sheet 44 extending outward in the transverse direction X beyond the respective lateral edges of the absorbent core 41 and the leakage-barrier sheet 43 are folded onto the side of the skin-facing surface in such a manner that the respective lateral portions may come close to each other toward the longitudinal imaginary center line P without overlapping the absorbent core 41.

The aforementioned lateral portions of the bottom sheet 44 exclusive of the gasket cuffs 70 may be folded toward the side of the skin-facing surface of the absorbent core 41 so as to define substantially Z-shaped cross-sections, respectively, and thereby to form the containment cuffs 80.

As a result of forming the containment cuffs 80 by folding the bottom sheet 44 in the manner as has been described above, an intermediate area of the skin-facing surface of the inner sheet 42 is defined between the opposite containment cuffs 80.

The gasket cuffs 70 are respectively provided with gasket elastics 71 secured between respective pairs of layers of the bottom sheet 44 locally folded in a Z-shape. As the gasket elastics 71, thread, string or strand elastics extending in the longitudinal direction Y are used. These gasket elastics 71 are secured under tension to the bottom sheet 44 so that the contractile force thereof may act on the gasket cuffs 70 in the longitudinal direction Y. For example, one to four gasket elastics 71 each having a fineness in a range of about 310 to about 1240 dtex are used and secured under tension at an elongation ratio in a range of about 2.3 to about 2.9 to the bottom sheet 44 so that contractile force may act on the gasket cuffs 70.

According to this embodiment, for example, three gasket elastics 71 are used for each of the gasket cuffs 70 on lateral portions in the transverse direction X of the absorbent core 41. According to this embodiment, as the gasket elastics 71, thread, string or strand elastics each having a fineness of about 470 dtex are used. Further, according to this embodiment, the gasket elastics 71 are secured under tension at an elongation ratio of about 2.7 to the bottom sheet 44 so that the contractile force thereof may act upon the gasket cuffs.

The gasket elastics 71 according to this embodiment do not extend to the front and rear ends 47, 48 of the crotch panel 40 but to the vicinities thereof. More specifically, as illustrated in FIGS. 2 and 3, ends 71*a* of the gasket elastics 71 on one side extend into the group of the front waist elastics 26 defining the front second elastic zone 26*b* and ends 71*b* of the gasket elastics 71 on the other side extend beyond the transverse imaginary boundary line L1 into the group of the rear waist elastics 36 defining the rear second elastic zone 36*b* which is adjacent to the buttocks covering portion 50.

In the respective gasket cuffs 70, the lateral edges of the leakage-barrier sheet 43 are interposed between the respective two layers defined by the folded lateral portions of the bottom sheet 44. In these folded lateral portions of the bottom sheet 44, the bottom sheet 44 and the leakage-barrier sheet 43 are joined to each other by bonding means 49a such as a hot melt adhesive.

In the respective containment cuffs 80, containment elastics 81 are provided between the respective two layers defined by the folded lateral portions of the bottom sheet 44. As the containment elastics 81, thread, string or strand elastics are used. These containment elastics 81 are secured under tension to the bottom sheet 44 so that the contractile force thereof may act upon the containment cuffs in the longitudinal direction Y. In the state illustrated in FIG. 8, the containment cuffs 80 are spaced away from the inner sheet 42 and come in close contact with the wearer's thighs under the effect of the contractile force of these containment elastics 81. The gasket cuffs 70 also bend under the effect of the gasket elastics 71 and come in close contact with the wearer's thighs. In the diaper 10 according to this embodiment, the containment cuffs 80 cooperate with the gasket cuffs 70 to form a dual barrier and thereby to prevent body waste such as urine and/or feces from leaking along the wearer's legs.

The buttocks covering portion 50 and the crotch panel 40 are joined to each other in a rear bonding zone 62 defined between the gasket cuffs 70 on the lateral edges in the transverse direction X of the absorbent core 41 but not joined to each other in rear non-bonding zones 64 defined so as to overlap the gasket cuffs 70. In FIG. 3, the rear bonding zone 62 is indicated by dots and the rear non-bonding zones 64 are indicated by crosses.

According to this embodiment, the rear non-bonding zones 64 are provided below the transverse imaginary boundary line L1 so as to be defined between an imaginary lines L2 extending in the longitudinal direction Y in parallel to the longitudinal imaginary center line P and lateral edges 40s of the crotch panel 40, respectively.

In the respective gasket cuffs 70 formed along the lateral edges 41s of the absorbent core 41, each of the imaginary lines L2 is preferably set at a distance in a range of about 5 to about 10 mm from the gasket elastic 71s of the plural gasket elastics 71 lying closest to the longitudinal imaginary center line P further toward this longitudinal imaginary center line P.

The regions subjected to the contractile force of the gasket elastics 71 are not limited to the regions in which the gasket elastics 71 are present but the regions in vicinities of these elastics 71 are also subjected to the contractile force of the gasket elastics 71. The regions subjected to the contractile force of these gasket elastics 71 may be varied depending on a correlation between the contractile force of these gasket elastics 71 and the stiffness of the bottom sheet 44 constituting the gasket cuffs 70. According to this embodiment, on the basis of dedicated research and consideration of the inventors, the rear non-bonding zones 64 are provided in consideration of the contractile force of the gasket elastics 71, the contractile force of the buttock elastics 51, the stiffness of the bottom sheet 44 constituting the gasket cuffs 70, and the stiffness of the rear waist inner and outer sheets 34, 35 constituting the buttocks covering portion 50. In this regard, the rear bonding zone 62 is preferably provided over the entire zone defined between the rear non-bonding zones 64.

As illustrated in FIG. 3, a zone in which the crotch panel 40 and the rear waist covering portion 12 overlap each other is provided with the rear bonding zone 65 in which the crotch panel 40 and the rear waist covering portion 12 are joined to each other.

As indicated by dots in FIG. 3, the rear bonding zone 65 is preferably provided over the entire zone in which the crotch panel 40 and the rear waist covering portion 12 overlap each other above the transverse imaginary boundary line L1 in the longitudinal direction Y.

As illustrated in FIG. 3, a zone in which the crotch panel 40 and the front waist panel 20 overlap each other is provided with the front bonding zone 61 in which the crotch panel 40 and the front waist panel 20 are joined to each other.

As indicated by dots in FIG. 3, the front bonding zone 61 is preferably provided over the entire zone in which the crotch panel 40 and the front panel 20 overlap each other.

These front and rear bonding zones 61, 62, 65 and the rear non-bonding zones 64 are provided between the bottom sheet 44 of the crotch panel 40 and the front and rear inner sheets 24, 34 of the front and rear panels 20, 30.

When the bottom sheet 44 of the crotch panel 40 is joined to the front and rear inner and outer sheets 24, 34 of the front and rear panels 20, 30, these sheets may be coated with hot melt adhesives in an omega-, wave- or stripe-pattern using a coater kept in contact with the sheets or kept not in contact with the sheets. For example, as illustrated in FIG. 6, the bottom sheet 44 of the crotch panel 40 and the rear inner sheet 34 of the buttocks covering portion 50 are bonded by bonding means 69 such as hot melt adhesives. It is not essential to apply hot melt adhesives as the bonding means 69 in omega-, wave- or stripe-pattern and it is also possible to coat the bonding zones 61, 62, 65 over the entire areas thereof with hot melt adhesives.

In this diaper 10, the buttocks covering portion 50 and the crotch panel 40 are not joined to each other in the transverse direction X at portions in which the gasket cuffs 70 are disposed and therefore it is possible to inhibit the contractile force of the gasket elastics 71 exerted upon the buttocks covering portion 50. In consequence, the contraction of the buttocks covering portion 50 in the longitudinal direction Y under the contractile force of the gasket elastics 71 can be inhibited and thereby undesirable decrease of an area adapted to cover the wearer's buttocks can be inhibited. In addition, the contractile force of the buttock elastics 51 exerted upon the absorbent core 41 can be inhibited and thereby a decrease of the area of the absorbent core 41 for absorption of body waste can be inhibited.

Moreover, the midsection of the absorbent core 41 defined between the gasket cuffs 70 along the lateral portions of the core 41 in the transverse direction X is joined to the buttocks covering portion 50 and whereby an unintentional movement of the absorbent core 41 relative to the buttocks covering portion 50 can be inhibited.

In addition, the rear waist elastics 36 are contractible along the lateral edges 41s in the transverse direction X and therefore the contraction of the absorbent core 41 in the transverse direction X can be inhibited. As a result a decrease of the area for absorption of body waste such as urine can be inhibited and thereby leakage of body waste out of the diaper 10 can be prevented.

In addition, the rear bonding zone 65 is provided in the zone in which the gasket elastics 71 and the rear waist elastics 36 intersect with each other and the rear waist covering portion 12 and the crotch panel 40 overlap with each other so that the rear waist covering portion 12 and the crotch panel 40 are joined to each other, and the front bonding zone 61 is provided in the zone in which the gasket elastics 71 and the front waist elastics 26 intersect with each other and the front panel 20 and the crotch panel 40 overlap with each other so that the front panel 20 and the crotch panel 40 are joined to each other. With such an arrangement, the front panel 20 and the rear waist covering portion 12 may be expanded in the transverse direction X to expand the crotch panel 40 also in the transverse direction X when the diaper 10 is put on the wearer's body. In this way, it is possible to enlarge the area of the absorbent core 41 serving to absorb body waste.

It should be appreciated that the embodiment illustrated in FIGS. 1 through 8 is one example of the embodiments and the present invention is not limited to this embodiment. For example, while the thread, string or strand elastics are used as the front and rear waist elastics 26, 36 in the illustrated embodiment, these elastics are not limited to such thread, string or strand elastics and it is also possible to replace them by sheet-like or belt-like elastics. This is true for the buttock elastics 51, the gasket elastics 71 and the containment elastics 81 also.

While the absorbent core 41 having the dimension in the transverse direction X in the midsection in the longitudinal direction Y smaller than that of the front or rear end is used in the illustrated embodiment as seen in FIG. 3, it is possible to use the absorbent core 41 having a uniform dimension in the transverse direction X. The configurations of the absorbent core 41 are not limited to these configurations.

While the buttocks covering portion 50 is configured to be rectangular in the illustrated embodiment, it is not essential for the rear lateral edges 31 and the rear inner end 33 to define square corners. For example, it is also possible to define round corners by curved lines contiguous to the rear lateral edges 31 and a curved line contiguous to the rear inner end 33.

While the rear bonding zone 62 is provided over the entire area defined between the rear non-bonding zones 64 provided in both lateral zones of the crotch panel 40 as a rectangular zone in the illustrated embodiment, the shape of the rear bonding zone 62 is not limited to the rectangular shape but may be shaped to be trapezoidal.

To avoid running off of adhesives in the course of bonding, the lateral edges 40s in the transverse direction X of the crotch panel 40 are preferably provided with non-bonding zones of about 5 mm in which the crotch panel 40 and the rear waist covering portion 12 are not joined to each other and, in addition to these non-bonding zones, with non-bonding zones in which the crotch panel 40 and the front panel 20 are not joined to each other. For the same reason, the inner end 23 of the front panel 20 in FIG. 3 is preferably provided with a non-bonding zone of about 5 mm in which the crotch panel 40 and the front panel 20 are not joined to each other and the inner end 33 of the rear waist covering portion 12 is preferably provided with a non-bonding zone in which the crotch panel 40 and the buttocks covering portion 50 are not joined to each other.

While the front waist elastics 26 and the rear waist elastics 36 have been described to include the same number of elastics, the present invention is not limited thereto but the number of the elastics may be different in the front and rear waist elastics 26, 36.

It is also possible to locate the lower end of the buttocks covering portion 50 above the gasket cuffs 70 and the containment cuffs 80.

The front and rear contractible zones 55, 56 may be provided symmetrically about the longitudinal imaginary center line P or asymmetrically about the longitudinal imaginary center line P.

Further, it is also possible to set the contractile force of the buttocks covering portion 50 to be substantially the same as the contractile force of the rear waist covering portion 12 in the transverse direction X. Specifically, it is possible to arrange so that, when a piece including a single buttock elastic 51 and a piece including a single rear waist elastic 36 both having a same dimension in the transverse direction X are cut out from the buttocks covering portion 50 and the rear waist covering portion 12, a dimension in the transverse direction X of the buttocks covering portion 50 in its contracted state is substantially the same as a dimension in the transverse direction X of the rear waist covering portion 12 in its contracted state. In this case, the intervals in the longitudinal direction Y of the buttock elastics 51 should be larger than the intervals in the longitudinal direction Y of the rear waist elastics 36.

In the overlapping zone of the buttocks covering portion 50 and the absorbent core 41, it is also possible to secure the buttock elastics 51 in a non-contracted state to the rear panel 30 so that the contractile force of this buttock elastics 51 may not act upon the rear panel 30 while, in the non-overlapping zone of the buttocks covering portion 50 and the absorbent core 41, the buttock elastics 51 are secured under tension to the rear panel 30 so that the contractile force of the buttock elastics 51 may act upon the rear panel 30. For example, as illustrated in FIG. 9, the overlapping zone of the buttocks covering portion 50 and the absorbent core 41 is provided with a contractile force-free zone 90 in which the contractile force of the buttock elastics 51 do not act thereon and the non-overlapping zone of the buttocks covering portion 50 and the absorbent core 41 is provided with a contractile force exerted zone 91 in which the contractile force of the buttock elastics 51.

By providing the zone 90 in this manner, it is possible to inhibit the contraction of the buttocks covering portion 50 in the transverse direction X and thereby to inhibit the decrease of the area of serving to absorb body waste such as urine. In addition to this measure, zones 91 may be provided on lateral portions in the transverse direction X of the zone 90 to ensure that the buttocks covering portion 50 conforms to the shape of the wearer's buttocks in the zones 91 and the wearer's buttocks are effectively covered with the buttocks covering portion 50. It is not essential to provide the contractile force-free zone 90 in the overlapping zone of the buttocks covering portion 50 and the absorbent core 41 and to provide the contractile force exerted zones 91 in the non-overlapping zones of the buttocks covering portion 50 and the absorbent core 41. For example, it is possible to provide the contractile force-free zone 90 having a dimension in the transverse direction X larger than or smaller than that of the absorbent core 41. The dimension in the transverse direction X of the contractile force exerted zones 91 may be varied depending on the dimension of the contractile force-free zone 90.

It is also possible to provide the contractile force-free zone so as to overlap the rear bonding zone 62 (See FIG. 3) and to provide the contractile force exerted zones 91 in a zone including the rear non-bonding zones 64 (See FIG. 3) and in a zone of the buttocks covering portion 50 exclusive of the contractile force-free zone 90.

To avoid the affection of the contractile force, for example, after the buttock elastics 51 have previously been arranged so as to extend between the rear waist lateral edges 31 in the transverse direction X, the elastics 51 may be cut in the contractile force-free zone 90 to be cut back or cut off or subjected to an elasticity deteriorating treatment or none of the elastics may be provided. It is also possible to secure the elastics 51 under no tension to the rear panel 30.

In this regard, it is also possible to secure the buttock elastics 51 in a non-contracted state over the entire area in the transverse direction X to the rear panel 30.

REFERENCE SIGNS LIST 10 disposable diaper (pants-type absorbent wearing article)
12 rear waist covering portion
20 front panel
26 front waist elastics
30 rear panel
36 rear waist elastics
40 crotch panel
41 absorbent core (absorbent area)
50 buttocks covering portion
51 buttock elastics
70 gasket cuffs
71 gasket elastics
X transverse direction
Y longitudinal direction
Z front-back direction

The invention claimed is:

1. A pants-type absorbent wearing article having a longitudinal direction, a transverse direction and a front-back direction, comprising:
   a front panel adapted to cover a front waist region of a wearer and having a dimension in the longitudinal direction extending between inner and outer ends of the front panel;
   a rear panel adapted to cover a rear waist region of the wearer; and
   a crotch panel including an absorbent structure and being connected to the front panel and the rear panel so as to cover a crotch region of the wearer, wherein
   the rear panel is formed with a rear waist covering portion and a buttocks covering portion contiguously extending downward from the rear waist covering portion and adapted to cover at least partially a wearer's buttocks, wherein:
   the rear waist covering portion has a dimension in the longitudinal direction that extends from the rear outer end of the rear panel to a transverse boundary line between the rear waist covering portion and the buttocks covering portion and the buttocks covering portion has a dimension in the longitudinal direction that extends from the transverse boundary line to the rear inner end of the rear panel;
   the dimension of the rear waist covering portion in the longitudinal direction is substantially the same as the dimension of the front panel;
   the absorbent structure includes an absorbent core extending in the longitudinal direction and gasket cuffs extending in the longitudinal direction along lateral portions of the absorbent structure and provided with gasket elastics adapted to be elastically contractible in the longitudinal direction; and
   the buttocks covering portion is provided with buttock elastics extending in the transverse direction, wherein
   the rear waist covering portion and the buttocks covering portion of the rear panel overlap with the absorbent core and the gasket cuffs of the absorbent structure,
   the rear waist covering portion is joined to the absorbent core and the gasket cuffs,
   the buttocks covering portion is joined to the absorbent core, and
   the buttocks covering portion is not joined to the gasket cuffs at a region where the buttocks covering portion and the gasket cuffs overlap with each other.

2. The pants-type absorbent wearing article according to claim 1, wherein:
   the rear waist covering portion is provided with rear waist elastics adapted to be elastically contractible in the transverse direction;
   the crotch panel and the rear panel are joined to each other at a zone in which the gasket elastics and the rear waist elastics intersect with each other;
   the front panel is provided with front waist elastics adapted to be elastically contractible in the transverse direction; and
   the crotch panel and the front panel are joined to each other at a zone in which the gasket elastics and the front waist elastics intersect with one another.

3. The pants-type absorbent wearing article according to claim 1, wherein the buttock elastics are secured under no tension to the rear panel.

4. The pants-type absorbent wearing article according to claim 1, wherein the buttock elastics are secured under no tension to the rear panel at least at a portion in which the buttocks covering portion and the absorbent structure overlap with each other.

5. The pants-type absorbent wearing article according to claim 2, wherein:
   both the buttock elastics and the rear waist elastics comprise a plurality of elastic threads elongated in the transverse direction under tension, and
   an elongation ratio of the buttock elastics is smaller than that of the rear waist elastics.

6. The pants-type absorbent wearing article according to claim 2, wherein:
   both the buttock elastics and the rear waist elastics comprise a plurality of elastic threads elongated in the transverse direction under tension, and
   an elongation ratio of the buttock elastics is equal to that of the rear waist elastics; and
   intervals in the longitudinal direction of the buttock elastics are larger than intervals in the longitudinal direction of the rear waist elastics.

7. The pants-type absorbent wearing article according to claim 2, wherein the rear waist elastics are contractible in the transverse direction in the lateral edges of the absorbent structure.

8. The pants-type absorbent wearing article according to claim 7, wherein a range in which the rear waist elastics are contractible in the lateral edges of the absorbent structure is 5 to 20% of the dimension in the transverse direction of the absorbent structure.

9. The pants-type absorbent wearing article according to claim 2, wherein,
   both the buttock elastics and the rear waist elastics comprise a plurality of elastic threads elongated in the transverse direction under tension, and
   an elongation ratio of the buttock elastics is smaller than that of the rear waist elastics.

10. The pants-type absorbent wearing article according to claim 2, wherein:
    both the buttock elastics and the rear waist elastics comprise a plurality of elastic threads elongated in the transverse direction under tension,
    an elongation ratio of the buttock elastics is equal to that of the rear waist elastics; and
    intervals in the longitudinal direction of the buttock elastics are greater than intervals in the longitudinal direction of the rear waist elastics.

* * * * *